US012595451B2

(12) United States Patent
Mann et al.

(10) Patent No.: US 12,595,451 B2
(45) Date of Patent: Apr. 7, 2026

(54) RAPIDLY DEPLOYABLE LAGOON COVER

(71) Applicant: BENNAMANN SERVICES LTD, Newquay (GB)

(72) Inventors: Christopher Mark Mann, Cornwall (GB); Tom Richard Taylor, Cornwall (GB)

(73) Assignee: BENNAMANN SERVICES LTD, Newquay (GB)

( * ) Notice: Subject to any disclaimer, the term of this patent is extended or adjusted under 35 U.S.C. 154(b) by 0 days.

(21) Appl. No.: 18/838,180

(22) PCT Filed: Feb. 13, 2023

(86) PCT No.: PCT/IB2023/051297
§ 371 (c)(1),
(2) Date: Aug. 13, 2024

(87) PCT Pub. No.: WO2023/152721
PCT Pub. Date: Aug. 17, 2023

(65) Prior Publication Data
US 2025/0115841 A1     Apr. 10, 2025

Related U.S. Application Data

(60) Provisional application No. 63/309,927, filed on Feb. 14, 2022.

(51) Int. Cl.
*C12M 1/00* (2006.01)
*C12M 1/09* (2006.01)
*C12M 3/00* (2006.01)

(52) U.S. Cl.
CPC ............ *C12M 23/38* (2013.01); *C12M 23/46* (2013.01); *C12M 23/56* (2013.01)

(58) Field of Classification Search
CPC ....... C12M 23/38; C12M 23/46; C12M 23/56
(Continued)

(56) References Cited

U.S. PATENT DOCUMENTS

| 2004/0055952 A1* | 3/2004 | Baumgartner ......... | C12M 23/36 |
| | | | 210/605 |
| 2008/0178739 A1* | 7/2008 | Lewnard ................ | C12M 21/02 |
| | | | 435/257.1 |

(Continued)

FOREIGN PATENT DOCUMENTS

| CA | 3024256 A1 | 5/2020 |
| DE | 10115623 A1 | 10/2002 |
| WO | 2022013796 A1 | 1/2022 |

OTHER PUBLICATIONS

International Preliminary Report on Patentability issued in corresponding Application No. PCT/IB2023/051297, dated Aug. 20, 2024 (7 pages).

(Continued)

*Primary Examiner* — Michael L Hobbs
*Assistant Examiner* — Lenora A Abel
(74) *Attorney, Agent, or Firm* — ROTHWELL, FIGG, ERNST & MANBACK, P.C.

(57) ABSTRACT

A cover for a slurry container is provided. The cover includes a plurality of attachable cover units including a first attachable cover unit and a second attachable cover unit. Each of the attachable cover units has at least one edge with an attachable portion. The first attachable cover unit is attached to the second attachable cover unit at the edge of the first and second attachable cover units having the attachable portion.

13 Claims, 15 Drawing Sheets

(58) Field of Classification Search
USPC ...................................................... 435/305.3
See application file for complete search history.

(56)                    References Cited

U.S. PATENT DOCUMENTS

2011/0287544 A1 * 11/2011 Berzin ................... C12M 23/56
                                                    435/257.1
2024/0034972 A1 * 2/2024 Mann ..................... C12M 23/38

OTHER PUBLICATIONS

International Search Report and Written Opinion issued in corresponding Application No. PCT/IB2023/051297, dated May 12, 2023 (10 pages).

* cited by examiner

1000

RAPIDLY DEPLOYABLE LAGOON COVER

CROSS REFERENCE TO RELATED APPLICATIONS

This application is a 35 U.S.C. § 371 National Stage of International Patent Application No. PCT/IB2023/051297, filed on Feb. 13, 2023, which claims priority to U.S. Provisional Patent Application No. 63/309,927, filed on Feb. 14, 2022, the disclosures of which are incorporated herein in their entirety by reference.

FIELD OF THE DISCLOSURE

This disclosure relates generally to covers for large surface areas that can be rapidly deployed.

BACKGROUND

Anaerobic digestion is a process that can be used to convert a wide range of biomass materials into mostly methane and carbon dioxide gases. Carbon dioxide ($CO_2$) can be used for a variety of purposes such as food and industrial processing. Methane, which is typically more valuable than carbon dioxide, can be used as a direct replacement for fossil fuels such as oil and natural gas. When methane is generated from anaerobic digestion from organic matter (i.e., biomass), it is often referred to as biomethane.

Biomethane can be used as a fuel (e.g., for combustion engines or fuel cells) to provide power and heat. When biomethane is burnt, the exhaust comprises only carbon dioxide and water. In principle, the quantity of carbon dioxide released equals the amount that would have been released had the biomass had been allowed to aerobically decompose naturally; therefore, methane produced in this way is effectively considered a zero-carbon fuel. The use of anaerobic digestion of biomass to produce methane is therefore seen as an effective way to reduce the level of carbon dioxide in the atmosphere and help to mitigate climate change. Patent Applications U.S. 63/052,190 and PCT/IB2021/056375, titled "Systems and Methods for Anaerobic Digestion," describe, for instance, an anaerobic digester.

SUMMARY

According to a first embodiment, a cover for a slurry container is provided. The cover includes a plurality of attachable cover units including a first attachable cover unit and a second attachable cover unit. Each of the attachable cover units has at least one edge with an attachable portion. The first attachable cover unit is attached to the second attachable cover unit at the edge of the first and second attachable cover units having the attachable portion.

According to a second embodiment, a system is provided. The system includes a slurry container. The system includes a cover for the slurry container. The cover includes a plurality of attachable cover units including a first attachable cover unit and a second attachable cover unit. Each of the attachable cover units has at least one edge with an attachable portion. The first attachable cover unit is attached to the second attachable cover unit at the edge of the first and second attachable cover units having the attachable portion.

According to a third embodiment, an attachable cover unit for a cover is provided. The attachable cover unit includes an expandable membrane having a top surface, a bottom surface, and edges, and wherein the expandable membrane is capable of storing gas. The attachable cover unit includes a first attachable portion coupled to a first edge of the expandable membrane.

BRIEF DESCRIPTION OF THE DRAWINGS

FIG. 6 and FIGS. 6A-6D illustrate a clamping arrangement 600 according to an embodiment.

DETAILED DESCRIPTION

Figure 1:
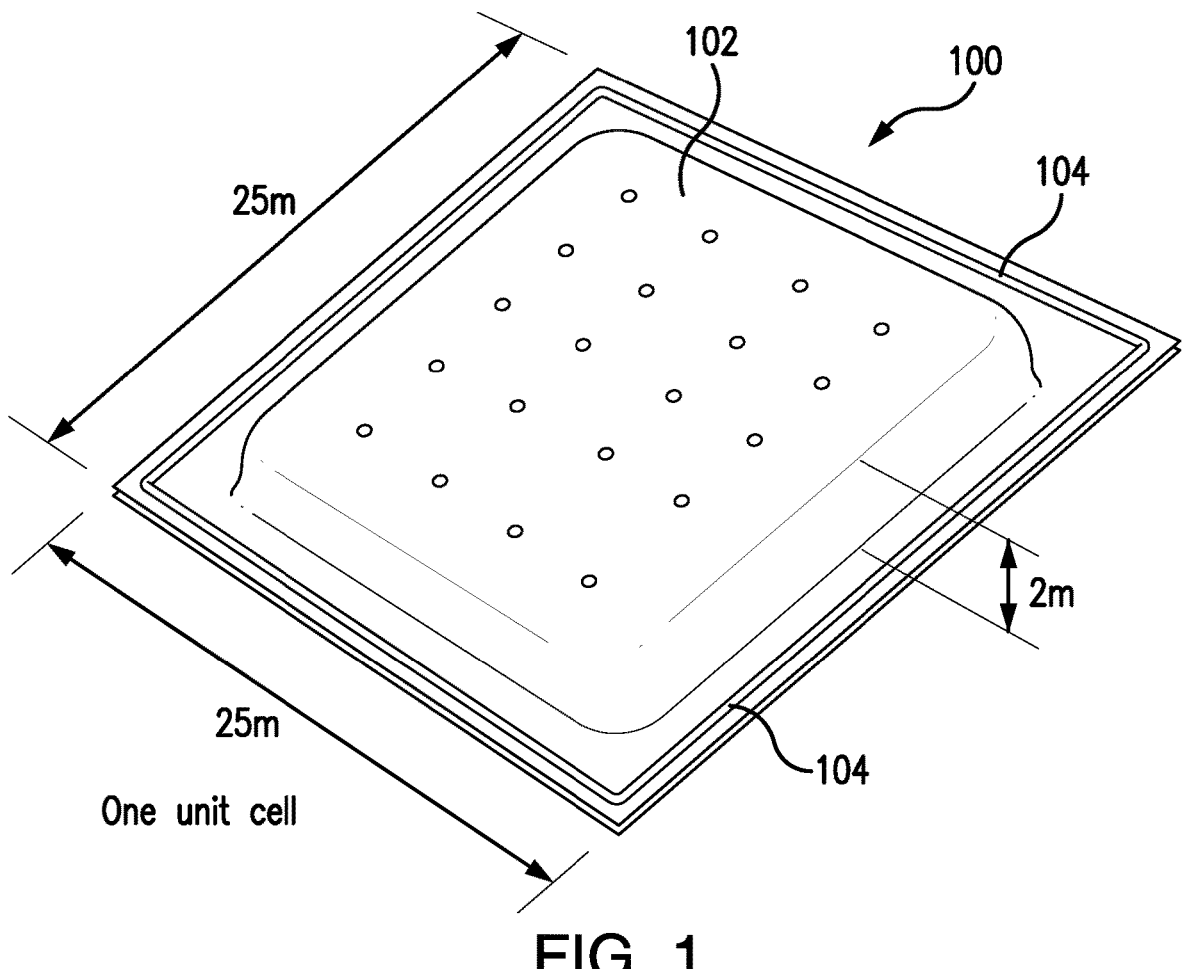
FIG. 1 illustrates a cover system according to an embodiment.

While aspects of the subject matter of the present disclosure may be embodied in a variety of forms, the following description and accompanying drawings are merely intended to disclose some of these forms as specific examples of the subject matter. Accordingly, the subject matter of this disclosure is not intended to be limited to the forms or embodiments so described and illustrated.

Unless defined otherwise, all terms of art, notations and other technical terms or terminology used herein have the same meaning as is commonly understood by persons of ordinary skill in the art to which this disclosure belongs. All patents, applications, published applications and other publications referred to herein are incorporated by reference in their entirety. If a definition set forth in this section is contrary to or otherwise inconsistent with a definition set forth in the patents, applications, published applications, and other publications that are herein incorporated by reference, the definition set forth in this section prevails over the definition that is incorporated herein by reference.

Unless otherwise indicated or the context suggests otherwise, as used herein, "a" or "an" means "at least one" or "one or more."

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, radial, axial, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of a device embodying aspects of the disclosure and are not intended to be limiting.

As used herein, the term "adjacent" refers to being near or adjoining. Adjacent objects can be spaced apart from one another or can be in actual or direct contact with one another. In some instances, adjacent objects can be coupled to one another or can be formed integrally with one another.

As used herein, the terms "substantially" and "substantial" refer to a considerable degree or extent. When used in conjunction with, for example, an event, circumstance, characteristic, or property, the terms can refer to instances in which the event, circumstance, characteristic, or property occurs precisely as well as instances in which the event, circumstance, characteristic, or property occurs to a close approximation, such as accounting for typical tolerance levels or variability of the embodiments described herein.

Many types of biomass can be anaerobically digested. To achieve the most beneficial impact with respect to climate change, using anaerobic digestion to limit or eradicate "fugitive" emissions of methane (such as those that are currently created by the poor management of animal manures such as cow and pig slurry in open lagoons) may be most effective. The use of open-slurry lagoons in the agriculture sector results in very high levels of fugitive methane emissions. By sealing the slurry lagoon to prevent aerobic digestion, the methane can be contained. This practice can be advantageous for the purposes of limiting or eradicating "fugitive" emissions of methane, and in embodiments disclosed herein can also provide for considerable operational benefits. Such benefits may include:

1) Reduced nitrogen loss; this is because nitrogen is contained in the digestate (i.e., the material remaining after the anaerobic digestion of the biomass), which can in turn reduce the need for fertilizer when the digestate is spread back onto the land.

2) Reduced handling and management of slurry; this is because rain water is prevented from entering the covered lagoon, meaning that the digestate is more concentrated and there is less to spread.

3) Reduced risk of overspill; this is because rain water is prevented from entering the covered lagoon, and in turn minimizes the possibility of leakage of raw slurry into waterways (which may be illegal in many countries).

4) Reduced greenhouse gases; this is because biomass (such as waste or spoiled animal feed) is usually managed by composting aerobically and the energy held in it is lost as heat during this process, and may result in large quantities of methane and nitrous oxides, both powerful greenhouse gases. Such greenhouse gases are reduced, however, with the use of a sealed slurry lagoon, such as provided by embodiments disclosed herein.

5) Reduced energy demands; this is because anaerobically generated methane may be used as fuel for a generator, e.g. to generate electricity and heat that can be used on the farm, thereby offsetting its electricity and energy usage.

Where the installation cost of a covered slurry lagoon is kept low, the above benefits can provide a reasonable return on investment for small-to mid-sized farms as compared to an open slurry lagoon.

However, because anaerobic digestion systems are often outdoors or otherwise exposed to natural elements (e.g., rain and snow), operation and monitoring of such systems may be difficult. Accordingly, there remains a need for improved anaerobic digestion systems and methods.

Methane fueled tractors are now in global production and other agricultural implements such as combine harvesters will rapidly follow. To ramp up fugitive methane capture to align with tractor production and roll out rates, a rapidly manufacturable and onsite deployable lagoon cover with biogas storage and processing will be advantageous.

For larger farms and correspondingly larger lagoons, trying to scale the cover size would become impractical due to its sheer size and weight. Larger lagoons require seam welding to stitch large sheets together which has to be done in the field in the outdoors environment using field welded seams. These are prone to debris ingress and inconsistent welds due to changes in temperature and rainwater etc., leading to seam failure and leaks of slurry and gas. This is not compatible with the high quality control demanded by environment agencies nor mass manufacture and commercial viability.

Mass manufacture of geomembrane lagoon covers will need patterning, cutting and seam welding of large geomembrane sheets which for reliability and repeatability must be carried out in a carefully controlled environment indoors. This effectively limits the size of a single lagoon cover that can be made, and similarly of tessellated lagoon panels such as those disclosed herein.

In order to capitalize on the fast rollout capability of mass produced methane tractors, a scalable mass manufacturing approach for lagoon covers with expandable storage must be adopted to ensure that there is sufficient methane capturing and processing capability in line with sales demand.

There is therefore a need for a quality controlled fabrication method to ensure rugged performance but that is also rapidly deployable using the minimum amount of lifting equipment and personnel. Embodiments proposed herein describe a tessellated cover, connecting multiple cover units or cells together. Reliably joining such large sheets and the connecting pipework presents a significant barrier to realising a tessellated and scalable lagoon cover system that can be deployed rapidly and yet also retractable as required for normal farm operations to continue.

According to embodiments, a tessellated scalable cover for a lagoon, and a system having a slurry lagoon and a cover for the slurry lagoon, are provided. These can have the benefits of:

1) Controlling the amount of rainwater that enters the lagoon, thereby minimizing the necessary size of the lagoon for an application.

2) A reusable and strong edge sealing system between adjacent covers that is quick to install and provides a liquid and gas tight seal between adjacent tessellated cover 'tiles.'

3) A liquid ballast tube system that simultaneously stiffens the lagoon cover, weighs the cover down and funnels the raw biogas into the biogas capturing pipework system.

4) A reticulated foam supported biogas capturing and channelling system that enables a semi-rigid form to be maintained yet allows biogas to flow freely.

5) A lagoon corner joining system where 2 or more sheet corners merge simultaneously and that clamps the extruded sheet edge seals and acts as a cross conduit through which the raw and cleaned biogas flows.

6) A rainwater collection sump that automatically seals once the water has been sucked out enabling the water in other sumps to continue to be withdrawn.

Other benefits include that the cover can capture, in some embodiments, 80%-100% of fugitive methane, depending on lagoon shape and edge conditions. Embodiments may also reduce rain loading, be retrofitted to any open slurry lagoon or pond (even grass banked), be cheap, stable in high winds, able to store significant volumes of cleaned biogas, may decrease slurry volumes for unloading and spreading, and utilize existing slurry handling. Embodiments may be long-lasting (e.g., for an XR5 geo-membrane or similar material, a 20-year lifetime can be expected), may be retrievable as a capital item making financing more readily available, and can get a farmer on the fugitive methane ladder, allowing the farmer to then invest in a full installation or slurry storage improvements. Embodiments may provide a scalable investment where the entire lagoon can be implemented in stages according to the revenues generated.

Other features and characteristics of the subject matter of this disclosure, as well as the methods of operation, functions of related elements of structure and the combination of parts, and economies of manufacture, will become more apparent upon consideration of the following description and the appended claims with reference to the accompanying drawings, all of which form a part of this specification, wherein like reference numerals designate corresponding parts in the various figures.

There is an urgent need to reduce the fugitive methane that is emitted from animal and human waste. In particular, the dairy and beef sectors are responsible for a significant fraction of fugitive methane from the agriculture sector and much of this is due to the fugitive emissions from open slurry lagoons.

Similarly, human excrement is responsible for a significant fraction of fugitive methane emitted through the anaerobic processes used in the wastewater treatment sector and, in particular, in the secondary digestion lagoons which are invariably open.

Unexpected flooding events are now becoming commonplace due to climate change and so there is also an urgent need to eradicate overspills from open lagoons.

U.S. Application No. 63/149,573, titled "Lagoon Cover," describes a novel floating lagoon cover that is able to capture and store biogas and that also enables the removal of rainwater. That application and the PCT application (PCT/IB2022/051297) claiming priority to that application are each incorporated by reference in their entirety herein. Even with such a novel floating lagoon cover, when the lagoon size is more than 25 metres square it becomes impracticable to manufacture, transport and install such a cover primarily due to its bulk and weight. One approach is to connect multiple lagoon covers together. However, in order to do so, the joints between covers should be as strong as the membrane and yet also be biogas- and water-tight. This would normally be achieved using a field weld using a hot air thermal wedge or RF heating wedge. This would result in a single large lagoon cover, but field welds are unreliable and the complete cover could not then be easily retracted or removed as required from time to time or if it needs to be recovered due to the finance not being paid. This last point is very important as a removable lagoon system can qualify for finance which then allows the farmer to spread the cost over several years enabling them to start to recover revenue from the use or the sale of the resulting methane.

In addition, the biogas handling pipework would rely on many separate pipe connections between the biogas storage cells, which would be overly complicated to install and then be prone to leaks at the joints when the lagoon cover is subject to high winds and the biogas storage bags move around.

This disclosure provides a solution to the above problems and results in rapidly deployable and removable floating lagoon covers that in principle can be scaled up without limit. As used herein, lagoon covers may be used for any type of slurry store or slurry container, including, without limitation, an earth banked lake, as well as circular steel tanks or concrete walled stores.

FIG. 1 illustrates a unit cell 100 of the tessellated lagoon cover system according to an embodiment. As shown, the unit cell 100 is a square slurry cover sheet, on which is positioned an expandable biogas storage bag (i.e., a gas store). A typical size is 25 m by 25 m, which is a size that can be readily handled during its manufacture and also transported and moved by just two field operatives. In this example, the expandable biogas storage bag may expand by up to 2 m. Other sizes and shapes are also possible. The unit cell 100 may be based on any lagoon cover, such as the lagoon covers disclosed in U.S. Application No. 63/149,573, or PCT/IB2022/051297, previously incorporated by reference, and is modified by including attachable portions 104 on one or more (and up to all) of the edges of the unit cell 100 so that the unit cell can attach to other unit cells 100 via the attachable portions 104. The attachable portions 104 are coupled to a main cover part 102 of the unit cell 100. The attachable portions 104 may also be referred to as locking edge strips.

The unit cell 100 may include any of the features disclosed in U.S. Application No. 63/149,573, or PCT/IB2022/051297, previously incorporated by reference, for example, including weighted ballast skirts and stiffening tubes, a gas processing unit, and a water collecting feature. Other aspects of the systems disclosed in U.S. Application No. 63/149,573, or PCT/IB2022/051297, previously incorporated by reference, are also applicable. However, as described herein, unit cell 100 may also include novel biogas capture and movement tubes which are built into the cover and can be connected into a network via corner joining clamps to enable the biogas from each unit cell 100 to be drawn out to the biogas drying and cleaning system and then pumped back into the storage compartments. For example, a skirt may surround the outer perimeter of the cover, such that the skirt is within the slurry container and is configured to stay submerged in slurry in the slurry container. The skirt may be weighted so that it remains submerged within the slurry container. There may also be a gas processing unit configured to process raw biogas from a gas outlet coupled to the slurry container and to feed processed biogas into a gas inlet of the cover. There may also be a water collecting area and a water outlet for allowing water on a top surface of an exterior of the cover to escape.

Figure 2:
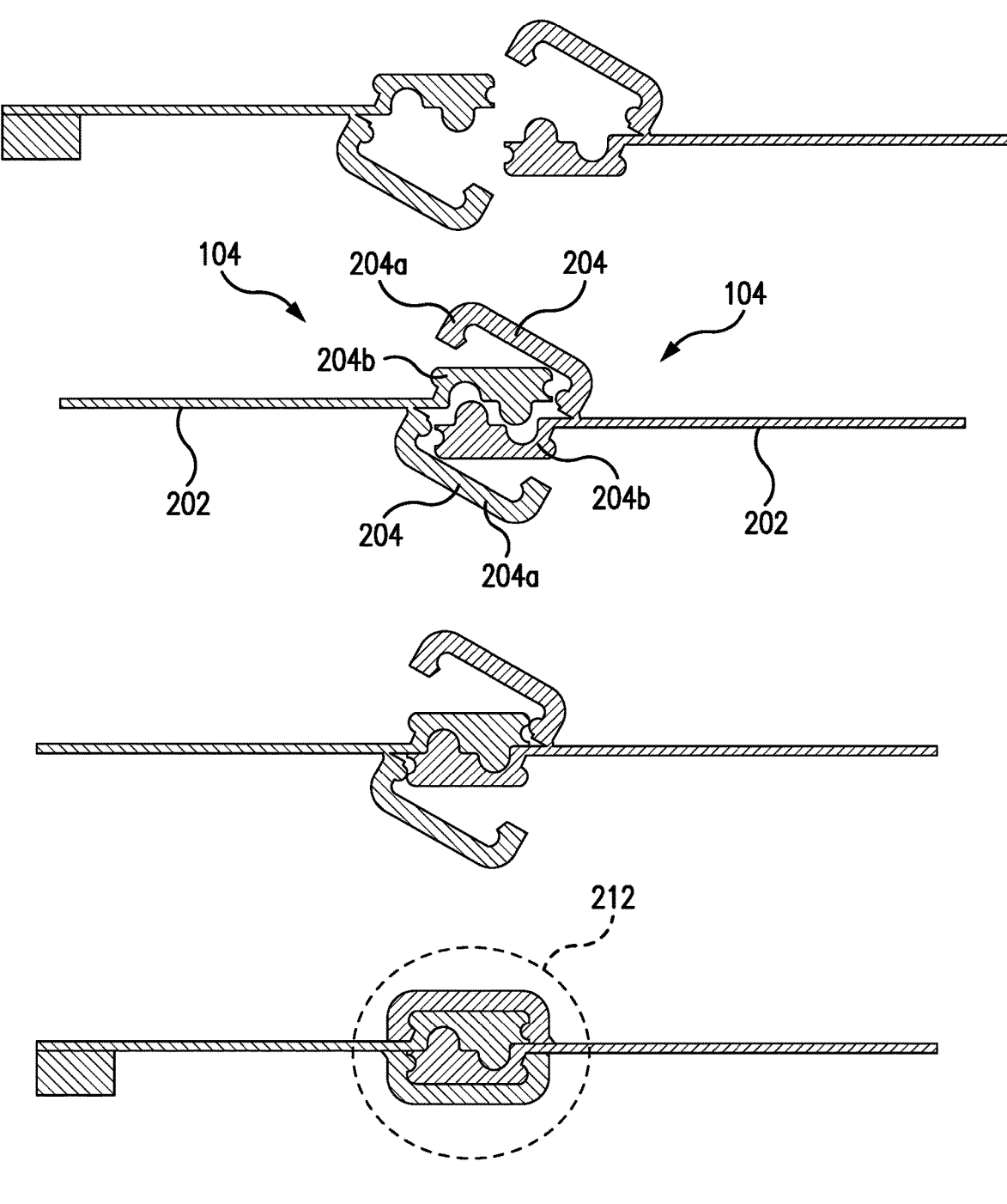
FIG. 2 and FIG. 2A illustrate aspects of a cover system according to an embodiment.
Figure 2A:
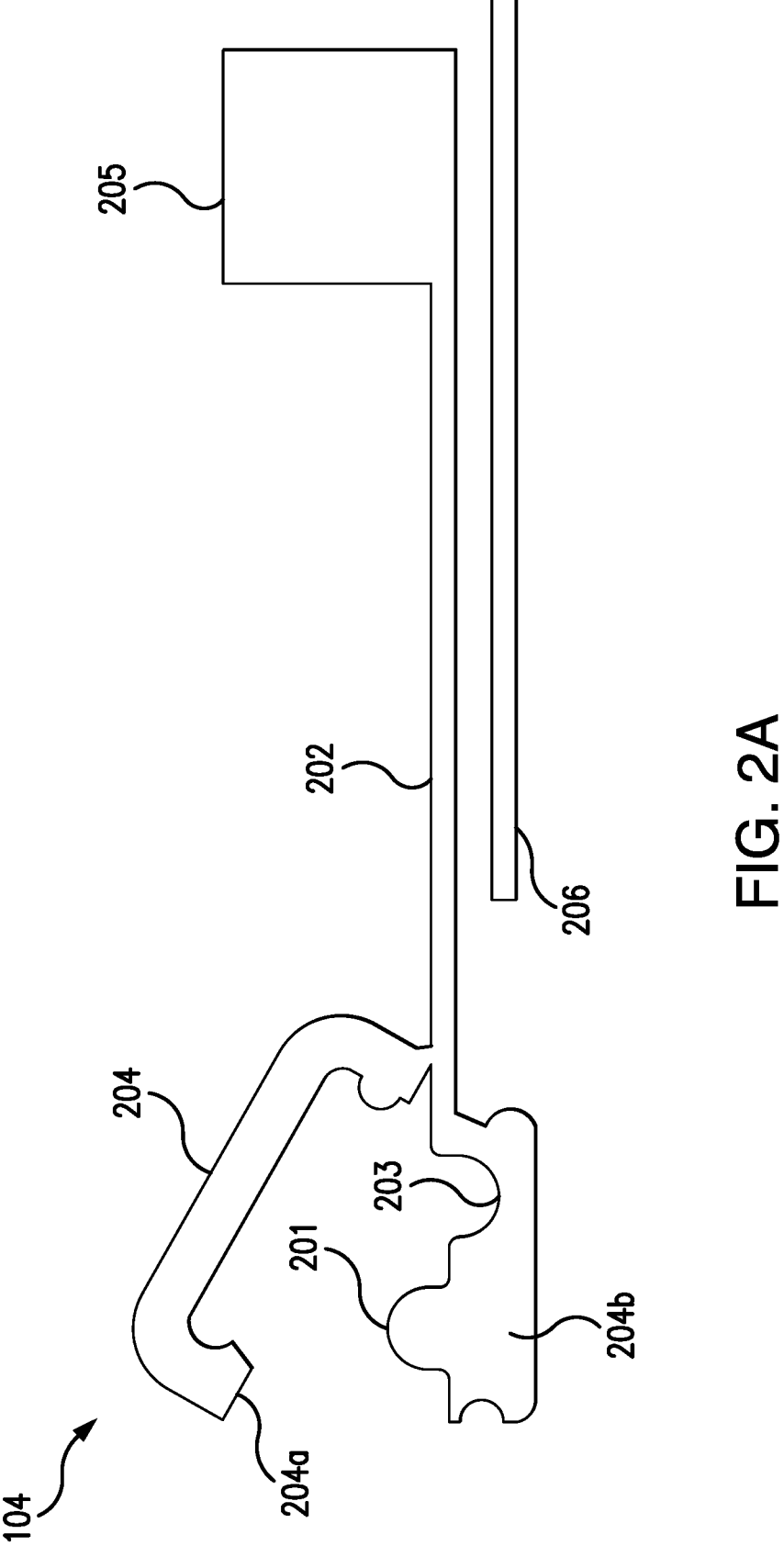

FIG. 2 and FIG. 2A illustrate an attachment portion 104 according to an embodiment. FIGS. 2 and 2A are cross sections taken along a plane orthogonal to an edge of the unit cell 100 shown in FIG. 1. As shown, attachment portion 104 may include a flat part 202, a clamp part 204, and block part 205. Clamp part 204 includes a top part 204a and a bottom part 204b. Clamp parts 204 of different attachment portions 104 may interfit with each other, clamping the attachment portions 102 together. For example, the bottom parts 204b may be irregular surfaces that interfit with each other, while the top parts 204a clamp around the bottom parts 204b of opposing clamp parts 204. As shown, the irregular surface of the bottom parts 204b includes at least one protruding portion 201 and at least one recessed portion 203. As shown, when locked, the clamp parts 204 of different attachment portions 104 may form an interconnected seam 212. The flat part 202 may be attached (e.g., welded) to a membrane 206 of the main cover part 102 of unit cell 100. In embodiments, this novel edge joining and clamping system may be formed from an extrusion, and is welded along each edge of the slurry cover membrane. The clamping system is designed to be at least as strong as the membrane and easily joined to it. As shown, the clamp parts 204 have bumps and crevices that interfit with each other and cause the respective attachment portions 104 of two attached attachment portions 104 to have a strong, secure connection. Other locking arrangements, e.g. based on different shapes or attachment mechanisms, are also possible.

The edge joining locking ribbon extrusion that forms attachment portions 104 can be made from a dissimilar material to the membrane 206 used for the slurry, provided the two materials are compatible with thermal or RF welding techniques. The same material may also be used, but in embodiments it can be advantageous to use a different material.

By using an extrusion process to form the edge joining and locking ribbon, the length that can be achieved is only limited by the size of the spool. In order to ensure that the ribbon lays flat on the spool, a reel space may be used that is the same thickness as the joining and locking feature. This edge can also be designed to act as a weld tool guide that would assist in an automated manufacturing process.

Figure 3:
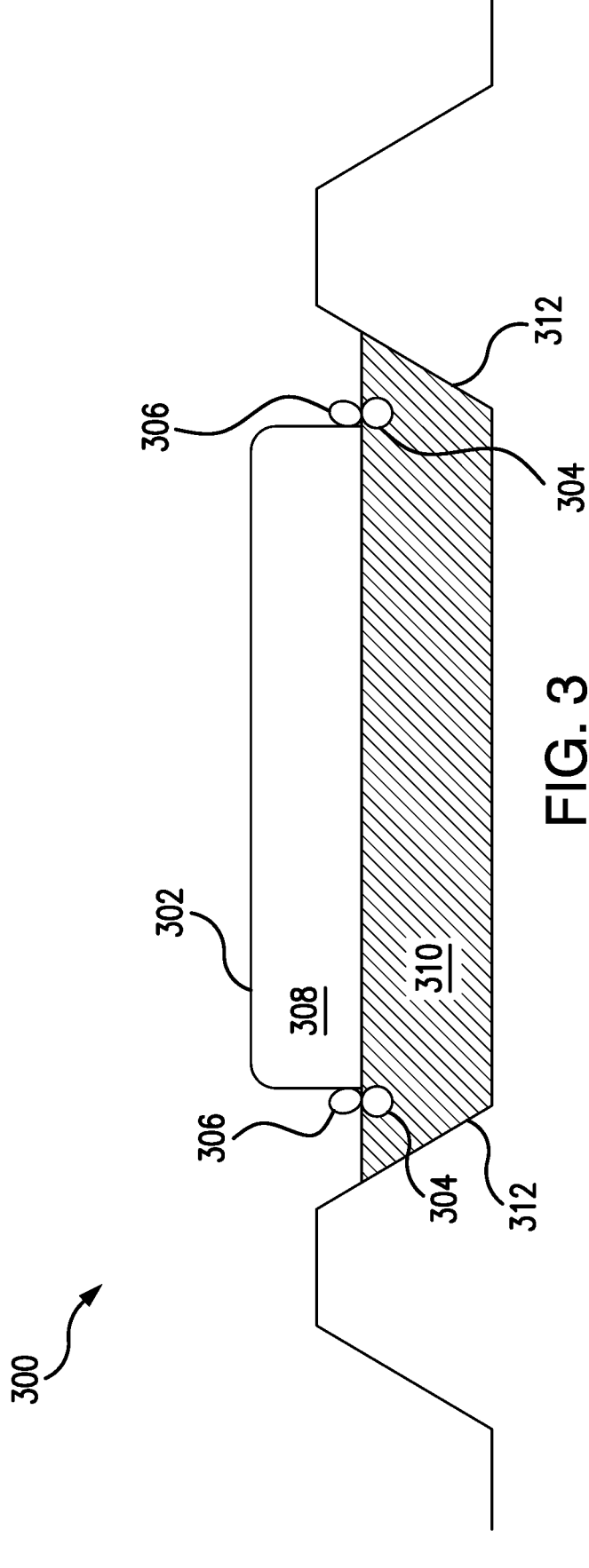
FIG. 3 illustrates aspects of a cover system according to an embodiment.

FIG. 3 illustrates a cross section through a single unit cell of a tessellated system 300 according to an embodiment. System 300 includes a tessellated cover 302, having a plurality of unit cells 100 attached to each other (one of which is shown), covering a slurry lagoon 310 (e.g., containing slurry) with banked sides 312. The tessellated cover 302 may include a biogas storage space 308 (e.g., containing cleaned biogas) within the cover 302. Two tubes are formed around the membrane of the cover 302, a ballast tube 304 and a gas tube 306. Ballast tube 304 is filled with water under slight pressure. This serves the purpose of acting as a stiffening frame and also a weighted ballast to hold the membrane onto the surface of the slurry during high wind conditions. It also acts to trap and guide the raw biogas into gas tube 306 that is mounted above the ballast tube 304, or alternatively cleaned biogas into the gas store. In embodiments, each unit cell 100 has gas tubes 306 and ballast tubes 304 around its perimeter.

Figure 4:
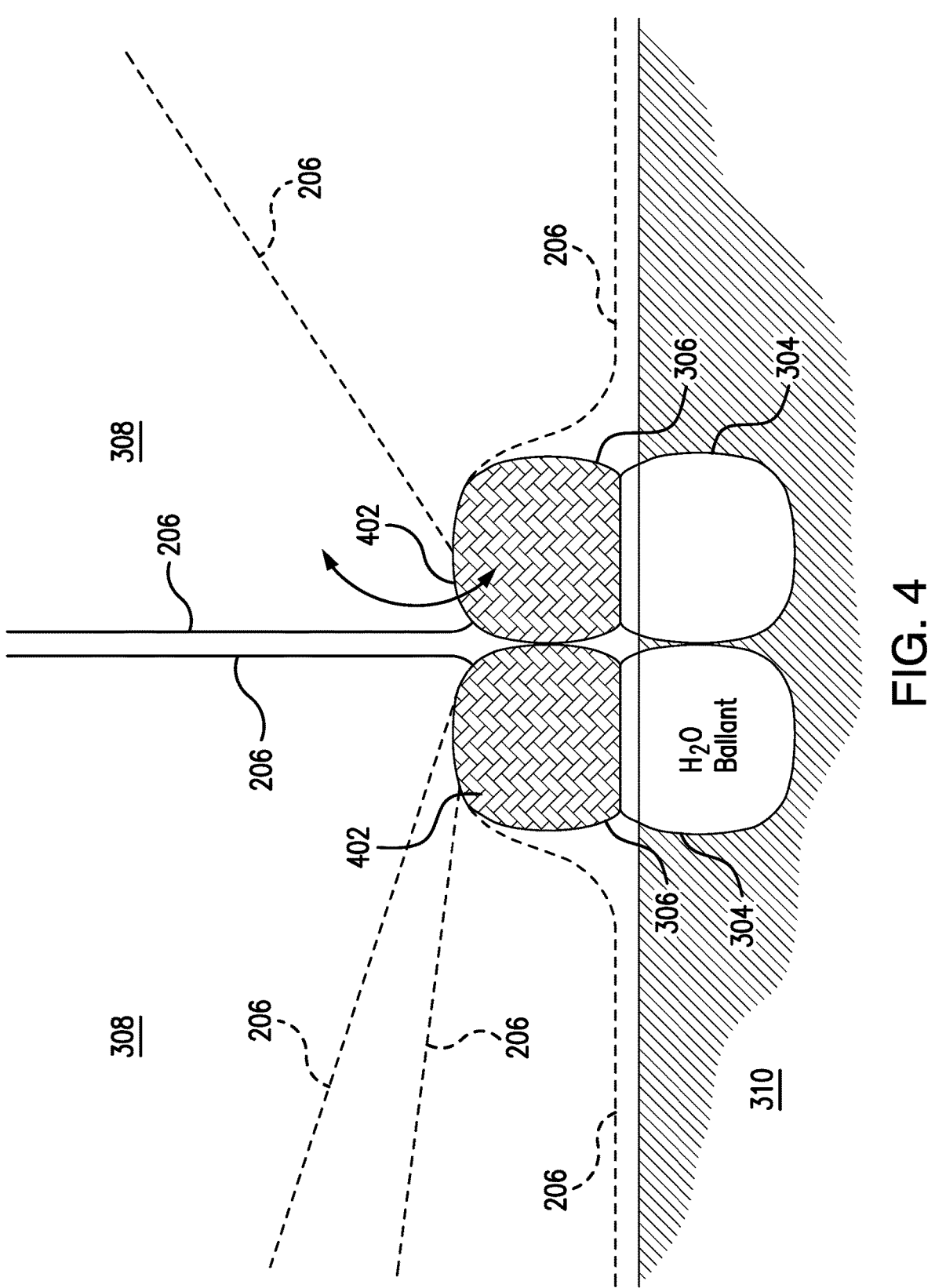
FIG. 4 illustrates aspects of a cover system according to an embodiment.

FIG. 4 illustrates a cross section through two adjacent unit cells of a tessellated system 300 according to an embodiment. Each of the unit cells 100 has a gas store 308 positioned above the slurry lagoon 310, and each of the unit cells 100 has a corresponding ballast tube 304 and gas tube 306. As shown, the gas tubes 306 include an opening or inlet 402 for the biogas to enter into the gas tubes 306. The gas tubes 306 for the system 300 form a network of raw gas tubes and a separate network of clean gas tubes. The opening 402 of the gas tube 306 shown on the left of FIG. 4 permits the gas from the slurry lagoon 310 to enter, and the opening 402 of the gas tube 306 shown on the right of FIG. 4 permits the gas from the gas store 308 to enter. Accordingly, the gas tube 306 shown on the left is part of the raw gas network and the gas tube 306 shown on the right is part of the clean gas network. The raw gas may be passed to a gas filtration system (GFS) for cleaning/filtering. The gas tubes 306 maintain their form through the use of a reticulated foam core that has sufficient structural rigidity but is sufficiently porous to allow the biogas to flow unrestricted. This prevents the tubes from collapsing, which could result in a loss of flow. The tubes may also be self-inflating and collapsible (e.g., vacuum collapsible), which facilitates deployment, transport, and retraction.

In order to hold the slurry cover membrane 206 in close contact with the surface of the slurry to aid stability in high wind conditions and also prevent the slurry from forming a crust, a slight vacuum is maintained by the biogas cleaning system (not shown). When all the raw biogas has been sucked out, the slurry cover membrane 206 is sucked down onto the reticulated foam filled biogas tube 306, effectively shutting the opening 402. This is illustrated with dashed lines, showing how the slurry cover membrane 206 is sucked down onto the reticulated foam filled biogas tube 306, effectively shutting the opening 402. This then ensures that the biogas from adjoining unit cells 100 is then preferentially drawn out. This prevents the situation where the biogas from one unit cell 100 builds up under the slurry cover and forms a bubble.

Figure 5:
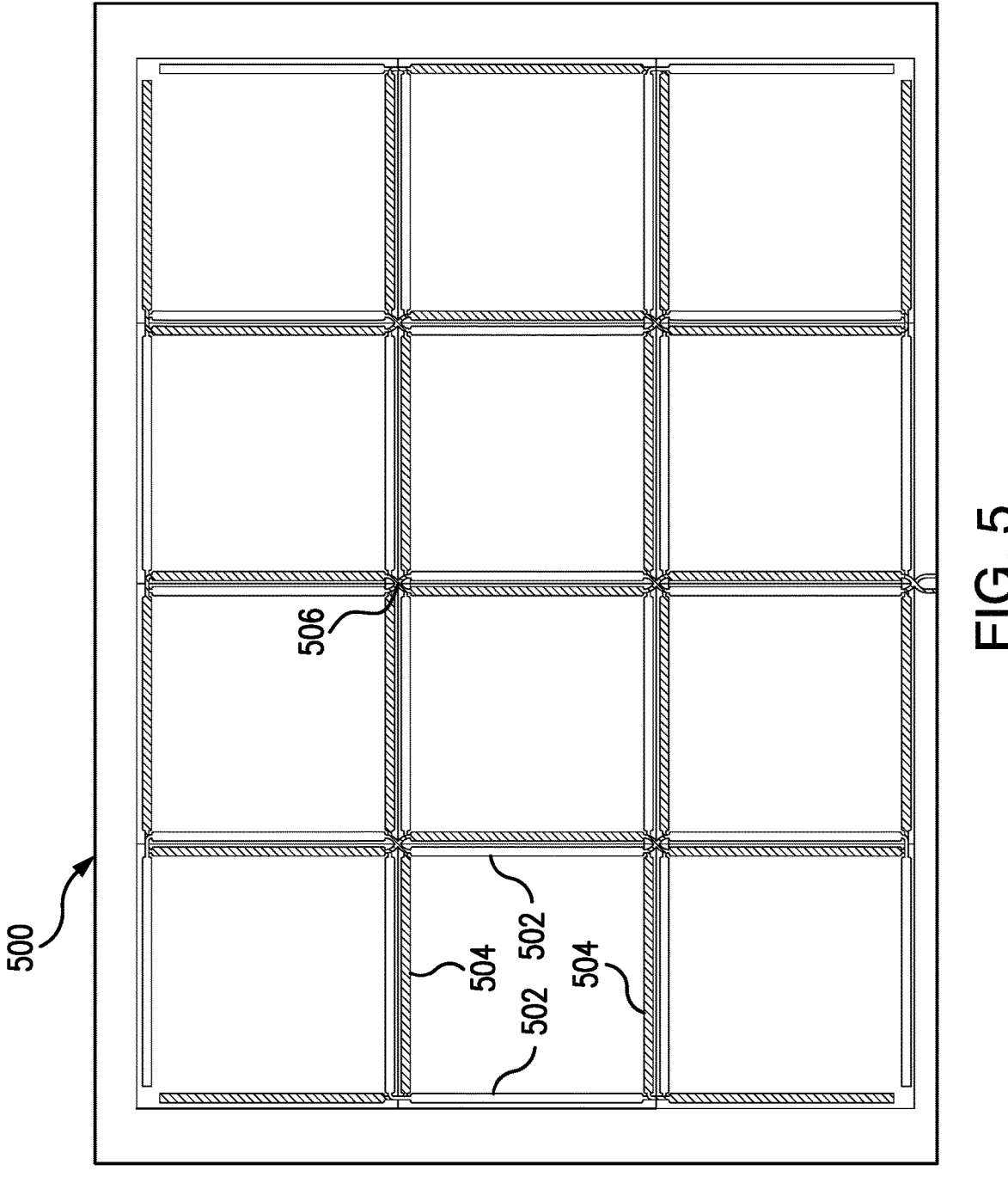
FIG. 5 illustrates aspects of a cover system according to an embodiment.

FIG. 5 illustrates a top view of a 3-by-4 tessellated cover system 500 according to an embodiment. It can be seen that the raw biogas flows through one tube network 502 (the collection of gas tubes 306 shown without cross hatching) and the cleaned biogas through a second tube network 504 (the collection of gas tubes 306 shown with cross hatching). The raw biogas and cleaned biogas networks are isolated from each other. As shown, each cell 100 has two parallel gas tubes 306 on opposing edges that are part of the raw gas network and two parallel gas tubes 306 on other opposing edges that are part of the clean gas network. Other shapes, configurations, and arrangements of the two tube networks are also possible.

Where two or more lagoon cover cells 100 are joined, the edge extrusion represents a weak point at which the ends could become separated and the slurry covers then become detached. Embodiments provide a clamping arrangement 506 that joins the pipes at the edges together, such as in the corners as shown in FIG. 5.

Figures 6A, 6B:
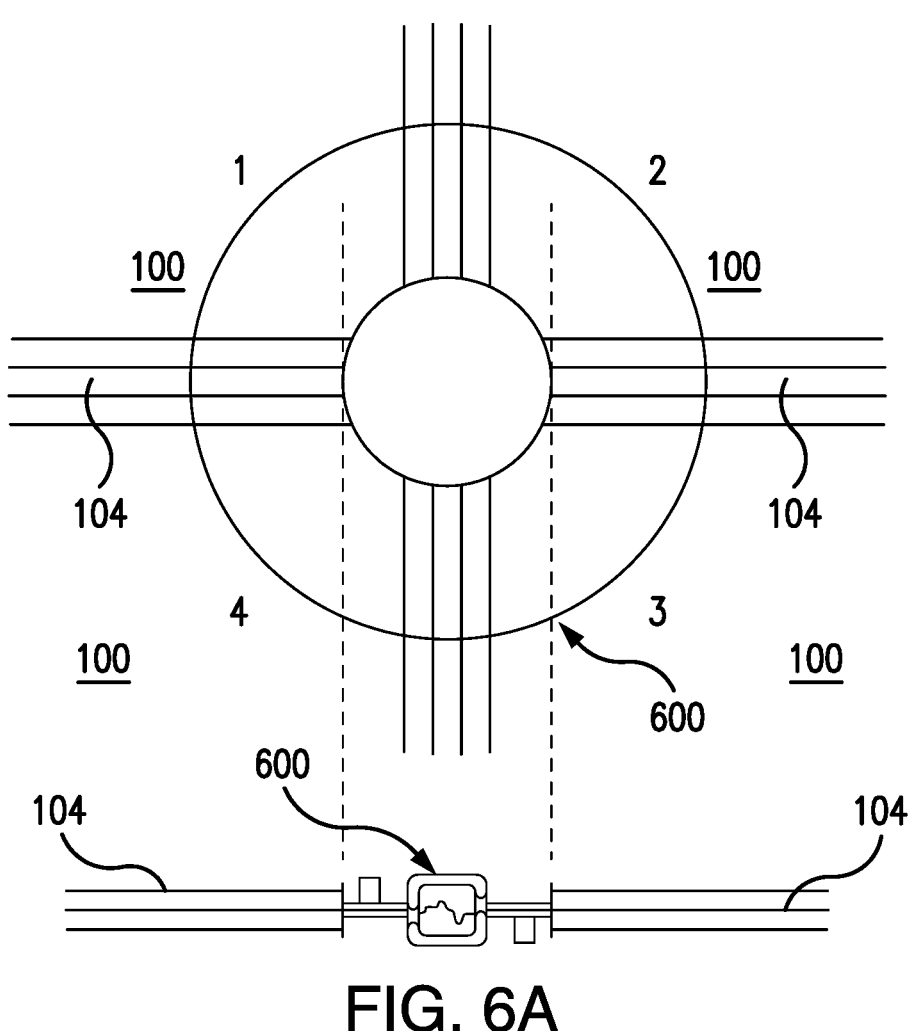
Figure 6D:
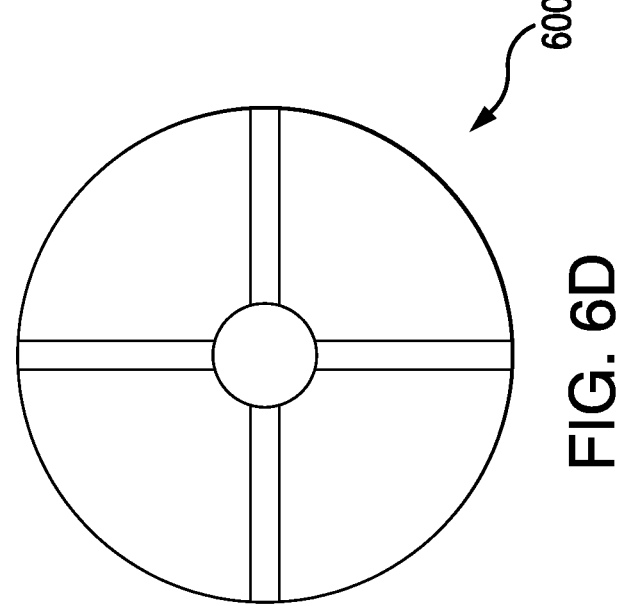
Figure 6C:
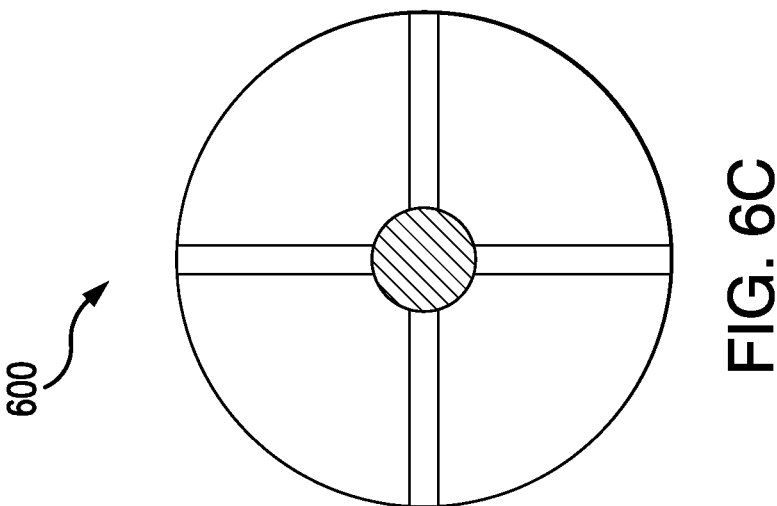

FIG. 6 and FIGS. 6A-6D illustrate a clamping arrangement 600 according to an embodiment. FIG. 6 illustrates a close-up region where four unit cells 100 meet, joined together by their respective attachment portions 104. FIG. 6A shows a cross-section of FIG. 6, as indicated by the dashed lines. FIG. 6B is a schematic diagram of a side view of the clamping arrangement 600, and FIGS. 6C and 6D are schematic diagrams of a top view of the clamping arrangement 600.

The edge locked extrusions (i.e., the attachment portions 104) are held in a channel positioned in the clamping arrangement 600, which may comprise a rigid injection moulded plastic disc, having a bottom disc 604 and a top disc 602. The plastic disc also has a threaded centre post 606, over which the top disc 602 with mirrored channels is fixed. A nut 608 is used to clamp the bottom disc 604 to the top disc 602 via the centre post 606. The threaded center post is shown in the top view of FIG. 6C (with cross hatching). The threaded center post is not shown in the top view of FIG. 6D (without cross hatching). In embodiments, the channels are slightly under sized such that some force is required to clamp the extrusion into them. Features such as ribs can also be positioned in the channels such that these help to seal any biogas and also dig into the extrusion edge to prevent it from being pulled backwards out of the clamp.

In some embodiments, as this joining system is formed from a rigid plastic, it can be designed to incorporate a pipe connection system that enables the biogas tubes 306 carrying the raw and cleaned biogas to be connected, greatly simplifying the raw and clean gas distribution network.

Figure 7:
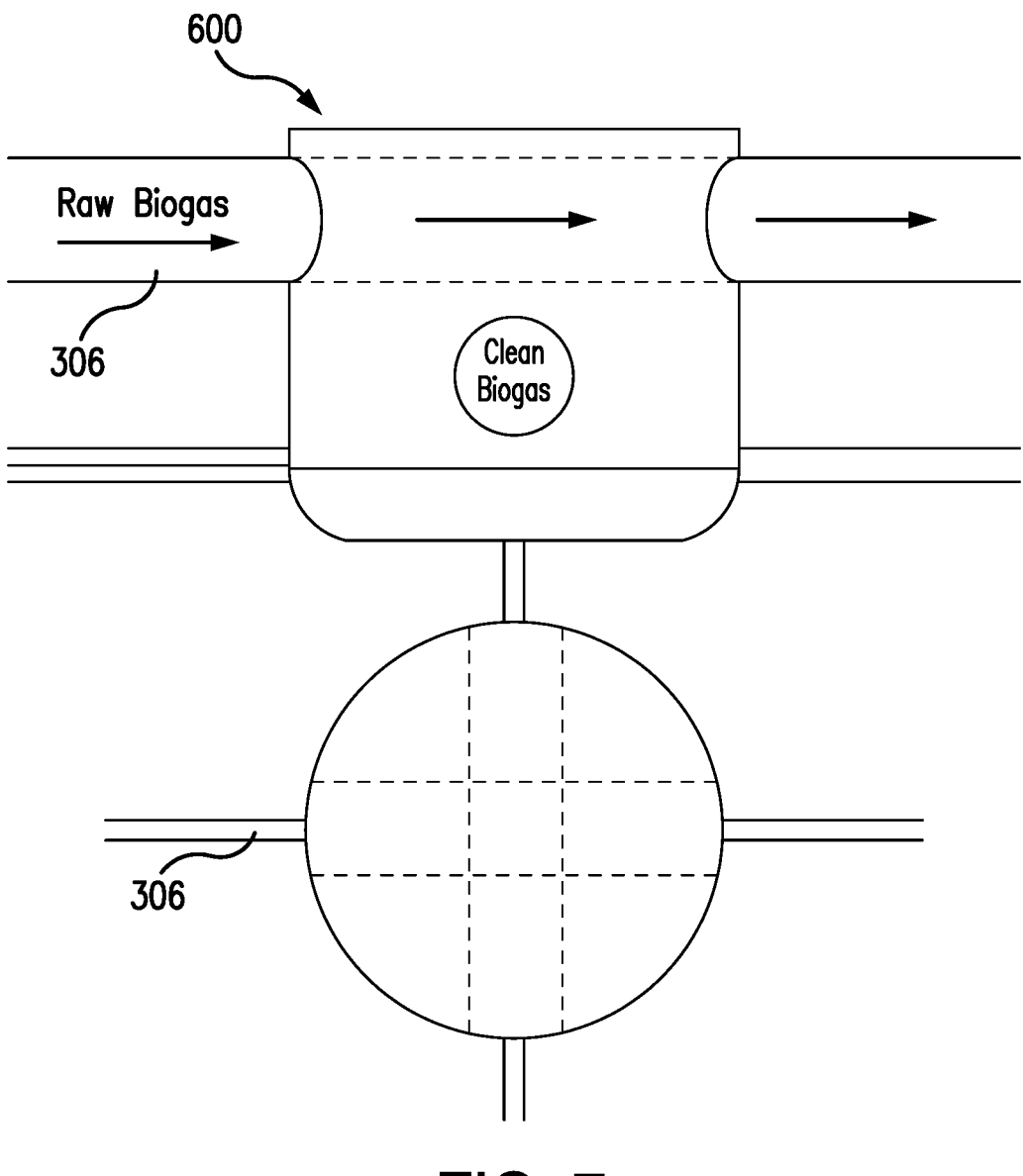
FIG. 7 illustrates a pipe connection system according to an embodiment.

FIG. 7 illustrates a pipe connection system according to an embodiment. As shown in top view, gas tubes 306 are able to pass through the clamping arrangement 600. The circled portion of FIG. 7 shows an enlarged view of the gas tubes 306.

Figure 8:
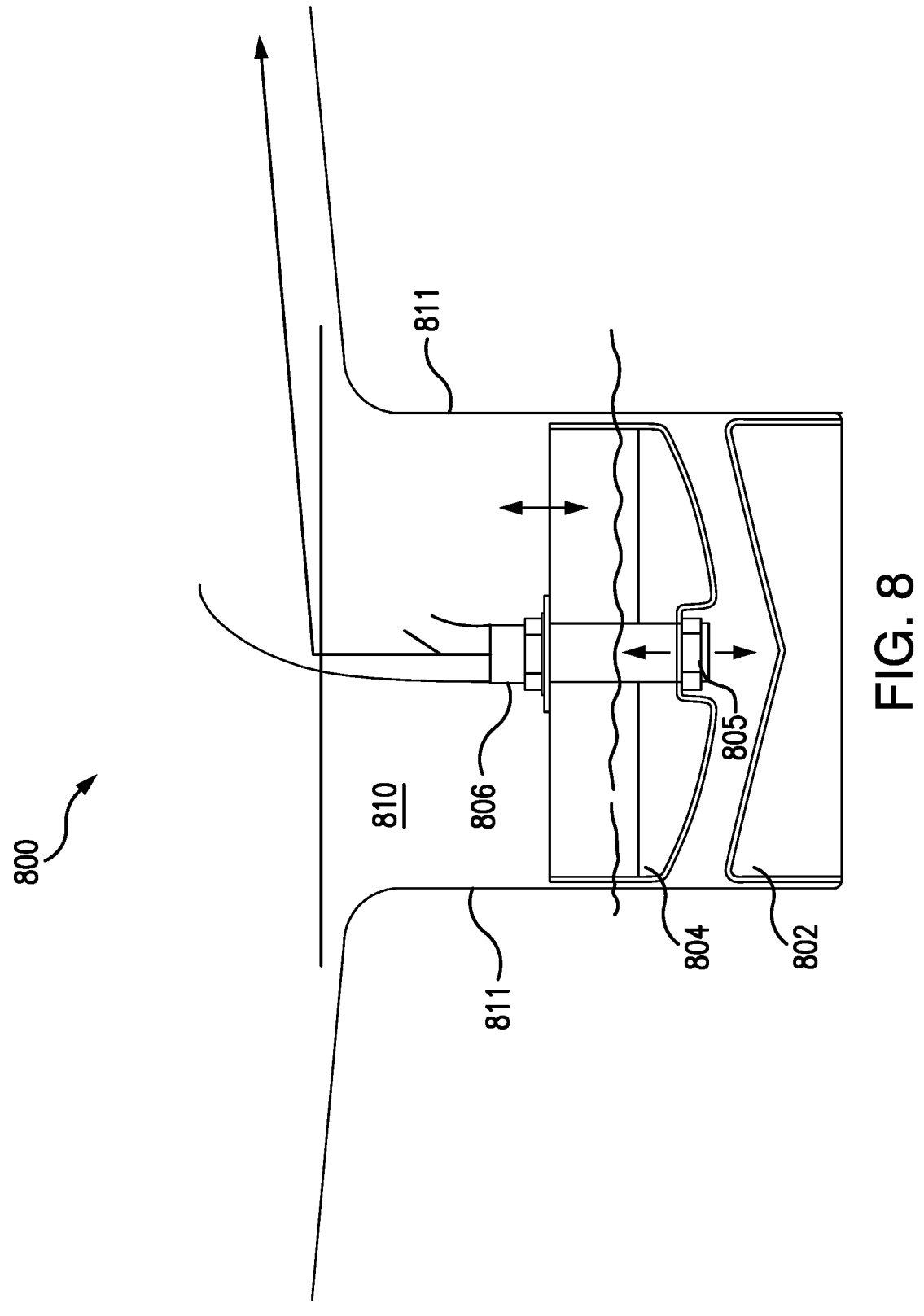
FIG. 8 illustrates a rainwater management system according to an embodiment.

FIG. 8 illustrates a rainwater management system 800 according to an embodiment. Rainwater handling is an important feature for a slurry lagoon cover. Proper rainwater management minimises the size that the lagoon needs to be in order to hold several months' worth of slurry, as is usually the legal requirement of environment agencies. It also provides the means to capture a valuable source of water that can be used on the farm or facility. For very large lagoons in flat areas it will be necessary to pump excess water out. In the same way that the biogas network provides the means to ensure a balanced draw of raw biogas from each cell 100, the same needs to be achieved for rainwater handling. In order to minimise the number of pumps required to draw off the water it is necessary to prevent air from getting into the pump line. One approach is illustrated by rainwater management system 800. Note that water collection approaches described in U.S. Application No. 63/149,573, or PCT/IB2022/051297, previously incorporated by reference, are applicable to this and other rainwater management embodiments.

A heavy weight 802 holds the sump 810 (having sides 811) upright in a well created in either the slurry cover or in the centre of the biogas store. Rainwater finds its way into the sump 810 through gravity. The weight 802 has a dished upper surface, typically conical. It could be formed using concrete, for example. A plastic dished shaped float 804 with the negative form of the dished surface of the concrete weight 802 houses the entrance 805 of the pipe 806 leading to the rainwater pump (not shown). When the water from that sump 810 is completely drained, the float's 804 lower surface shuts off the entrance 805 to the outlet pipe 806, causing the suction from the rainwater pump to shift to another sump in the rainwater collection network (not shown). This process continues until the last sump is dry at which point the suction at the pump increases. This increase in suction could be used as a trigger to shut the pump off. Each cell 100, or a subset of the cells 100, may have a rainwater pump associated with it.

A simple float switch in one or more of the rainwater sumps could be used to switch the pump on when the level rises above a certain height. As rainwater handling is important for successful operation of the lagoon in some embodiments, a backup circuit is usually included. This could be another pump that runs from its own dedicated power supply such as a stand-by generator that automatically starts if there is a loss of power from the mains network.

Figure 9:
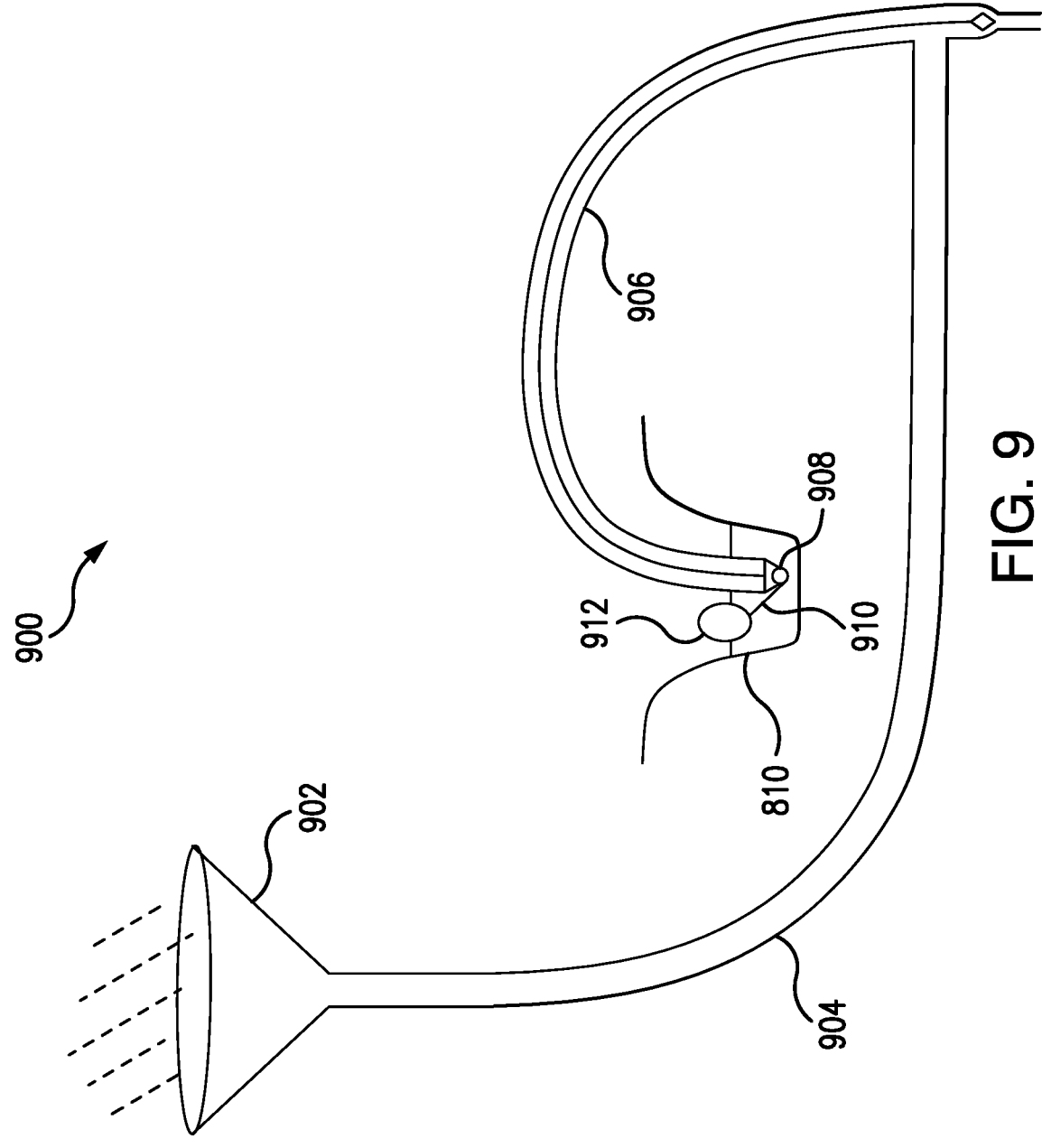
FIG. 9 illustrates an automatic syphoning system according to an embodiment.

FIG. 9 illustrates a novel automatic syphoning system 900. This system is useful in particular in areas where there is a sufficient fall of precipitation. This system has the advantage that it is effectively switched on by rainfall and powered by gravity. It therefore has no control requirements and is therefore effectively failsafe.

A high entrance area rain catching reservoir 902 is positioned higher than the highest point of the lagoon, which is usually the bund wall. The rain reservoir 902 is sized such that it catches a much larger volume of rain that the volume of the exit pipe 904 and the pipe 906 leading up to the sump 810, which is positioned on the lagoon liner. This ensures that as soon it starts to rain, the exit pipe 904 from the rain catcher quickly fills and runs into the sump drain pipe 906. The sump drain pipe 906 exit is held closed by a tapered plug 908 situated in a tapered exit plug hole. The tapered plug 908 is made from a heavy material such as lead. A stainless steel cable 910 is attached to the exit plug 908 and this cables 910 runs up the internal bore of the sump drain pipe 906. The other end of the cable 910 runs around a pulley and is attached to a float 912 positioned in the sump 810. As the rain fall continues, the sump exit pipe 906 is filled from its bottom, which is the lowest position in the system. The sump 810 also starts to fill with rainwater falling on the slurry cover. As the sump exit pipe 906 is filled from the bottom, eventually it passes over the lagoon bund wall height and then continues to fill the sump 810. The float 912 is designed to provide sufficient lift to pull the exit plug 908 from its tapered seat. When the height of water reaches a predetermined point set by the length of cable 910, the exit plug 908 is lifted and the column of water above now has sufficient weight to start a gravity powered syphon which continues until the float's 912 height drops and the sealing plug 908 falls back into place. The process repeats until the rain stops.

It is important that the lagoon cover requires as little maintenance as possible compared to that required for an open slurry lagoon. An open slurry lagoon occasionally requires stirring and this is usually carried out by the farmer using a propeller type stirring blade affixed via a long propeller shaft connected to the rear power take off of a tractor. The tractor is then reversed down an access ramp and the stirrer pushed into the slurry. The power take off is engaged and the stirrer moves the slurry away from the ramp pushing back into the lagoon, fresh slurry is drawn in to replace it, and a slow gyration of the slurry ensues. A similar process is used when the lagoon needs emptying. A large hose connected to a power take off driven slurry pump is pushed into the lagoon. The pump is then engaged and used to draw slurry out into a slurry tanker.

Figures 10A, 10B:
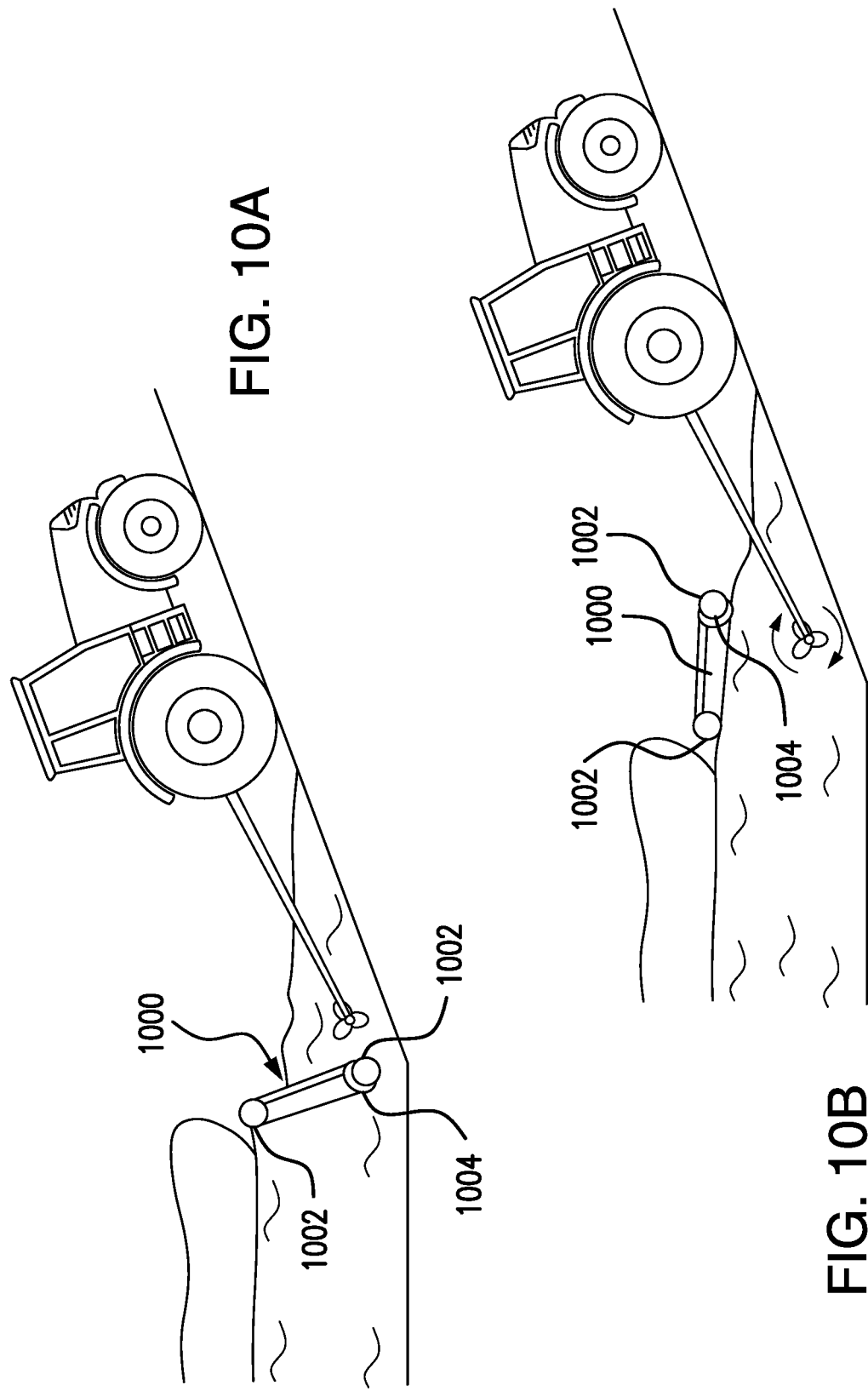
FIGS. 10A-10D illustrate using a tractor to stir the covered lagoon system according to an embodiment.
Figures 10C, 10D:
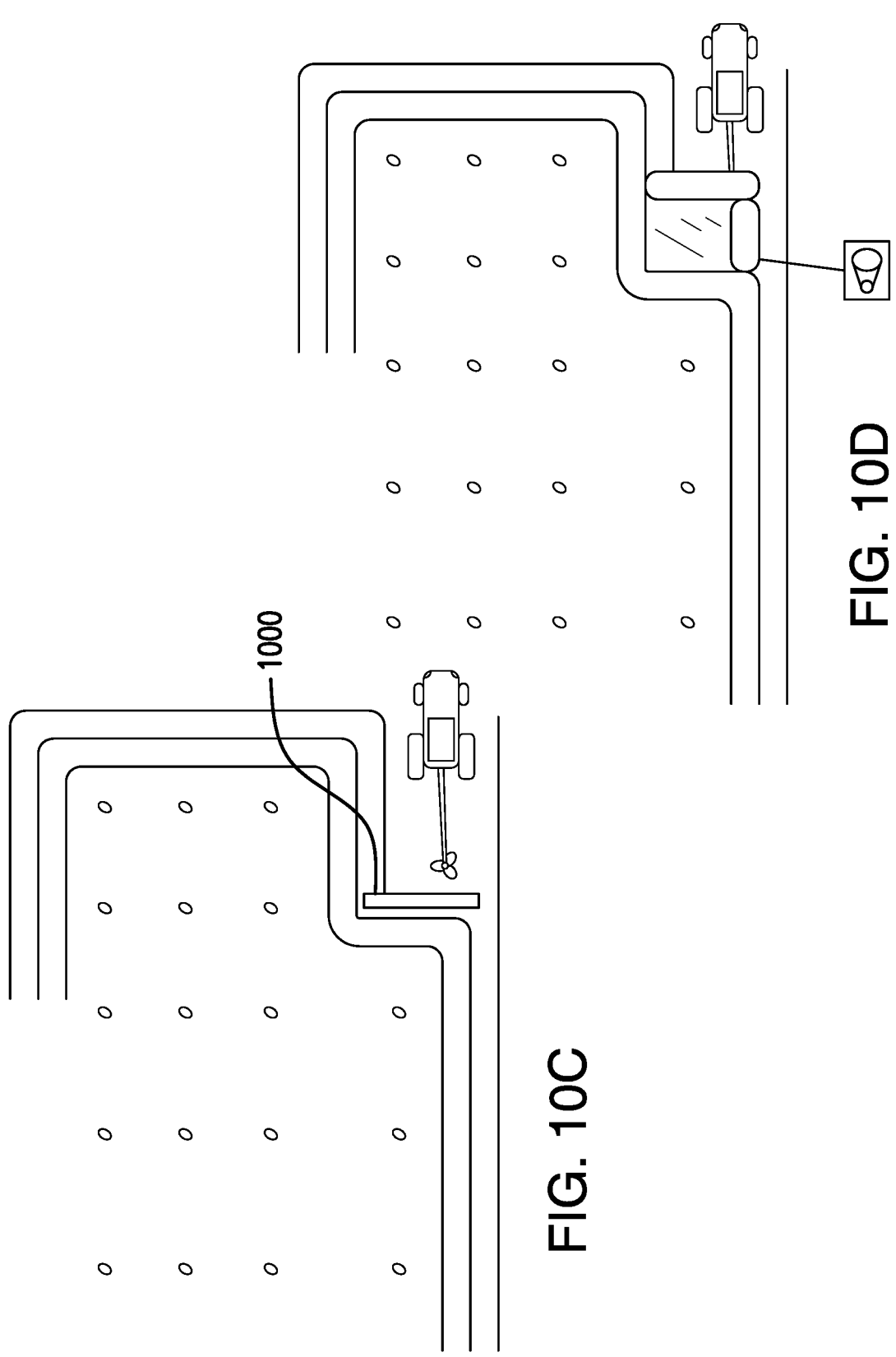

FIGS. 10A-10D illustrate using a tractor to stir the covered lagoon system according to an embodiment. In embodiments, the lagoon is provided with an opening in the cover. To provide access at the bottom of the ramp, a liftable side skirt or flap 1000 is provided to ensure the biogas remains sealed in. The skirt 1000 is held in its normal down position (e.g., as shown in FIGS. 10A, 10C) by a weighted bag 1004. When the farmer requires access for stirring or emptying, air is forced into one or more inflation bags 1002 sized to provide sufficient lift to raise the weighted bag 1004 (e.g., as shown in FIGS. 10B, 10D). The farmer is then provided access to the slurry in the main lagoon. The weighted skirts and edge sealing systems disclosed in U.S. Application No. 63/149,573, or PCT/IB2022/051297, previously incorporated by reference, are also applicable to this embodiment.

Figure 11:
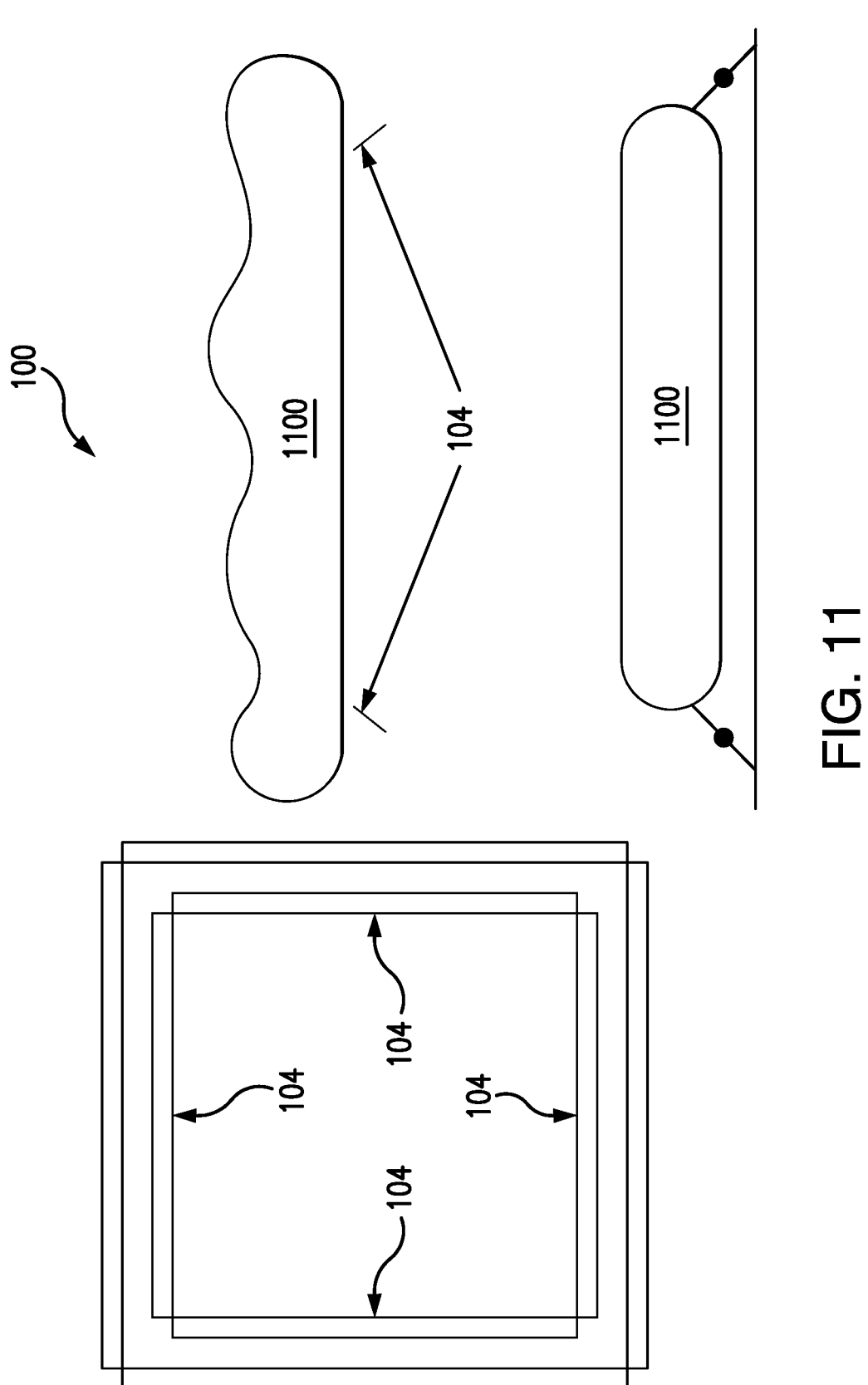
FIG. 11 illustrates a unit cell with a cover system according to an embodiment.

FIG. 11 illustrates a unit cell 100 with a biogas storage bag 1100 attached to it according to an embodiment. For minimal additional manufacturing cost, the slurry cover can incorporate one half of the extruded edge during its manufacture in positions where a gas store bag can be attached at a later date. This offers a number of advantages, one of which is that the farmer can purchase only what can be affordable or as required according to regulations as they are updated. For example, a very low cost lagoon cover that only provides rainwater handling and gas capture but not storage could be purchased. This would be suitable for a lagoon that produces so much biogas that a full time biogas processing is commercially justified. In this instance, the methane can then being used continuously or alternatively processed and stored as compressed or liquid methane for onsite use or sale. Alternatively, a cover system could be configured so that some storage is present for only fraction of the lagoon surface area. The base top slurry lagoon cover is the same as in other embodiments.

Figure 12:
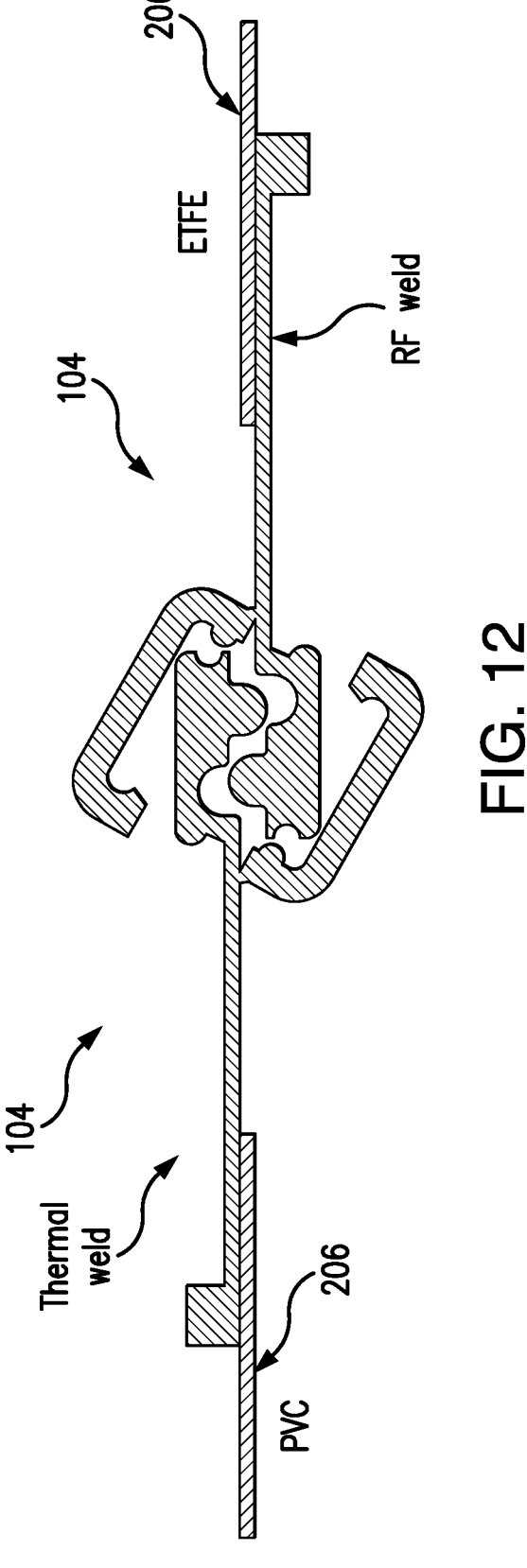
FIG. 12 illustrates aspects of a cover system according to an embodiment.

FIG. 12 illustrates attachable portions 104 joining two unit cells 100 having a membrane 206 of different material to each other. Another advantage of this approach is that certain polymers cannot be welded together and so the entire lagoon cover system must be made from the same material even though the material for the biogas storage compartment could use a much cheaper material than the material that is in contact with the slurry and needs to be more chemically resistant. This is true for Poly Vinyl Chloride (PVC) and Ethylene Tetrafluoroethylene (ETFE). These two systems offer different benefits but cannot be welded together due to their different properties. However, the extruded edge seal allows two sheets from these very different materials to be joined. The extruded edge seal relies on the physical fit of the two halves. These can be extruded for each different material and then welded to each respective sheet using whichever joining process is appropriate (e.g., thermal weld, RF weld). This then allow the two sheets to be joined together even though it is not possible to weld them.

While various embodiments of the present disclosure are described herein, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

One or more embodiments are further described below. Embodiments:

A1. A tessellated cover for a slurry container (e.g., lagoon), the tessellated cover comprising:

a plurality of attachable cover units including a first attachable cover unit and a second attachable cover unit, wherein each of the attachable cover units has at least one edge with an attachable portion;

wherein the first attachable cover unit is attached to the second attachable cover unit at the edge of the first and second attachable cover units having the attachable portion.

A2. The tessellated cover of embodiment A1, wherein the attachable portion of the first attachable cover unit interfits with the attachable portion of the second attachable cover unit, thereby clamping the first and second attachable cover units together.

A2a. The tessellated cover of embodiment A2, wherein the attachable portion of the first attachable cover unit includes a first top part and a first bottom part, the attachable portion of the second attachable cover unit includes a second top part and a second bottom part, and the first bottom part interfits with the second bottom part, the first top part clamps over the second bottom part, and the second top part clamps over the first bottom part, forming an interconnected seam.

A2b. The tessellated cover of embodiment A2a, wherein the first bottom part and the second bottom part each include at least one protruding portion and at least one recessed portion.

A3. The tessellated cover of any one of embodiments A1-A2, A2a, and A2b, wherein each edge of each of the attachable cover units has an attachable portion that is attached to another one of the attachable cover units.

A4. The tessellated cover of any one of embodiments A1-A3, wherein the attachable portions of the attachable cover units are welded onto the attachable cover units.

A4a. The tessellated cover of any one of embodiments A1-A3, wherein the attachable portions are formed via an extrusion process.

A5. The tessellated cover of any one of embodiments A1-A4, and A4a, wherein the plurality of attachable cover units includes additional attachable cover units, and the additional attachable cover units are attached to one another to cover the slurry container (e.g., lagoon).

A6. The tessellated cover of any one of embodiments A1-A5, further comprising:

a ballast tube around the perimeter of each of the attachable cover units; and a gas tube around the perimeter of each of the attachable cover units.

A7. The tessellated cover of embodiment A6, wherein the gas tube is positioned above the ballast tube.

A8. The tessellated cover of any one of embodiments A6-A7, wherein the gas tube comprises a reticulated foam core that is porous to allow biogas to flow through the gas tube.

A9. The tessellated cover of any one of embodiments A6-A8, wherein the gas tube forms a first tube network for raw biogas and a second tube network for cleaned biogas.

A10. The tessellated cover of any one of embodiments A6-A8, further comprising a disc having channels and positioned between at least the first and second attachable cover units that clamps the attachable portions of the first and second attachable cover units between a top disc part and a bottom disc part, wherein the attachable portions are fitted within the channels of the disc.

A10a. The tessellated cover of embodiment A10, wherein the disc includes a post and a nut threadedly engaged with the post to clamp the disc.

A11. The tessellated cover of any one of embodiments A10 and A10a, wherein the disc is positioned at a corner of each of the first and second attachable cover units and two additional attachable cover units.

A12. The tessellated cover of any one of embodiments A10-A11, wherein the gas tube passes through the disc.

A13. The tessellated cover of any one of embodiments A1-A12, further comprising a biogas storage bag connected to one of the attachable cover units.

A14. The tessellated cover of embodiment A13, wherein the attachable cover units are made of a first material and the biogas storage bag is made of a second material different from the first material.

A15. The tessellated cover of any one of embodiments A1-A14, further comprising:

a sump positioned in an open portion of the one or more attachable cover units for collecting rainwater;

piping for removing the rainwater;

a sump pump coupled to the piping;

a weight positioned near a bottom of the sump and having a dished upper surface; a float having a lower surface designed to interfit with the dished upper surface of the weight, wherein the float houses an entrance of the piping, such that when the rainwater from the sump is drained the lower surface of the float shuts off the entrance to the piping and when the rainwater from the sump is not drained the lower surface of the float permits the rainwater to flow into the entrance to the piping.

A15a. The tessellated cover of any one of embodiments A1-A14, further comprising:

a sump positioned in an open portion of the one or more attachable cover units for collecting rainwater;

a rain catching reservoir positioned higher than the highest point of the slurry container (e.g., lagoon);

a first exit pipe for the sump;

a second exit pipe for the rain catching reservoir coupled to the first exit pipe for the sump;

a tapered plug situated in a tapered exit plug hole and coupled to the first exit pipe for the sump;

a cable attached to the tapered plug;

a float positioned in the sump, wherein one end of the cable is attached to the float and another end of the cable is attached to the first exit pipe for the sump.

A16. The tessellated cover of any one of embodiments A1-A15, and A15a, wherein one or more of the attachable cover units is according to any of the embodiments disclosed in Appendix A (including, e.g., the embodiments of a cover claimed therein).

B1. A system comprising:

a slurry container (e.g., slurry lagoon); and a tessellated cover for the slurry container (e.g., slurry lagoon), the tessellated cover comprising:

a plurality of attachable cover units including a first attachable cover unit and a second attachable cover unit, wherein each of the attachable cover units has at least one edge with an attachable portion;

wherein the first attachable cover unit is attached to the second attachable cover unit at the edge of the first and second attachable cover units having the attachable portion.

B1'. The system of embodiment B1, wherein the tessellated cover for the slurry container (e.g., slurry lagoon) is any one of embodiments A2-A16.

B2. The system of any one of embodiments B1 and B1', further comprising a skirt around the perimeter of the tessellated cover.

B3. The system of embodiment B2, further comprising a weighted bag to hold down the skirt, and inflatable bags capable of lifting the skirt when inflated.

C1. A method for retrofitting an uncovered slurry container (e.g., slurry lagoon) with a cover, the method comprising:

installing a cover on an uncovered slurry container (e.g., slurry lagoon), wherein the cover is any one of embodiments A1-A16.

C2. The method of embodiment C1, further comprising attaching each of the plurality of attachable cover units to one or more of the other attachable cover units.

C3. The method of any one of embodiments C1-C2, further comprising filling the ballast tube with water, circulating gas from the first tube network for raw biogas into a gas processing system to clean the gas, and circulating the cleaned gas to the second tube network for clean biogas.

D1. An attachable cover unit for a tessellated cover, the attachable cover unit comprising:

an expandable membrane having a top surface, a bottom surface, and edges, and wherein the expandable membrane is capable of storing gas; and a first attachable portion coupled to a first edge of the expandable membrane.

D2. The attachable cover of embodiment D1, wherein the first attachable portion includes a top part and a bottom part.

D3. The attachable cover of embodiment D2, wherein the bottom part includes at least one protruding portion and at least one recessed portion.

D4. The attachable cover of any one of embodiments D1-D3, further comprising additional attachable portions coupled to the remaining edges of the expandable membrane.

D5. The attachable cover of any one of embodiments D1-D4, wherein the attachable portions are welded onto the attachable expandable membrane.

D6. The attachable cover of any one of embodiments D1-D5, wherein the attachable portions are formed via an extrusion process.

D7. The attachable cover of any one of embodiments D1-D6, further comprising:

a ballast tube around the perimeter of the expandable membrane; and a gas tube around the perimeter of the expandable membrane.

D8. The attachable cover of embodiment D7, wherein the gas tube is positioned above the ballast tube.

D9. The attachable cover of any one of embodiments D7-D8, wherein the gas tube comprises a reticulated foam core that is porous to allow biogas to flow through the gas tube.

D10. The attachable cover of any one of embodiments D1-D9, wherein the attachable cover includes features of any of the embodiments disclosed in Appendix A (including, e.g., the embodiments of a cover claimed therein).

E1. A method of using a slurry container (e.g., slurry lagoon), the method comprising:

providing a system according to any one of embodiment B3;

positioning a tractor with a stirrer near the slurry container (e.g., slurry lagoon);

inflating the inflatable bags to cause the skirt to lift;

inserting the stirrer into the slurry container (e.g., slurry lagoon); and stirring the slurry container (e.g., slurry lagoon).

The invention claimed is:

1. A cover for a slurry container, the cover comprising:

a plurality of attachable cover units including a first attachable cover unit and a second attachable cover unit, wherein each of the attachable cover units has a cover portion and at least one edge with an attachable portion different from the cover portion;

wherein the first attachable cover unit is attached to the second attachable cover unit at the edge of the first and second attachable cover units having the attachable portion so that the attachable portion of the first attachable cover unit attaches to the attachable portion of the second attachable cover unit.

2. The cover of claim 1, wherein the attachable portion of the first attachable cover unit interfits with the attachable portion of the second attachable cover unit, thereby clamping the first and second attachable cover units together.

3. The cover of claim 1, wherein the attachable portion of the first attachable cover unit includes a first top part and a first bottom part, the attachable portion of the second attachable cover unit includes a second top part and a second bottom part, and the first bottom part interfits with the second bottom part, the first top part clamps over the second bottom part, and the second top part clamps over the first bottom part, forming an interconnected seam.

4. The cover of claim 3, wherein the first bottom part and the second bottom part each include at least one protruding portion and at least one recessed portion.

5. The cover of claim 1, wherein each edge of each of the attachable cover units has an attachable portion that is attached to another one of the attachable cover units.

6. The cover of claim 1, further comprising:

a ballast tube around a perimeter of each of the attachable cover units; and a gas tube around the perimeter of each of the attachable cover units;

wherein the gas tube is positioned above the ballast tube.

7. The cover of claim 6, wherein the gas tube comprises a reticulated foam core that is porous to allow biogas to flow through the gas tube;

wherein the gas tube forms a first tube network for raw biogas and a second tube network for cleaned biogas.

8. The cover of claim 6, wherein the attachable cover units are made of a first material and the biogas storage bag is made of a second material different from the first material.

9. The cover of claim 1, further comprising a disc having channels and positioned between at least the first and second attachable cover units that clamps the attachable portions of the first and second attachable cover units between a top disc part and a bottom disc part, wherein the attachable portions are fitted within the channels of the disc, wherein the disc includes a post and a nut threadedly engaged with the post to clamp the disc.

10. The cover of claim 1, further comprising a biogas storage bag connected to one of the attachable cover units.

11. The cover of claim 1, further comprising:

a sump positioned in an open portion of the one or more attachable cover units for collecting rainwater;

piping for removing the rainwater;

a sump pump coupled to the piping;

a weight positioned near a bottom of the sump and having a dished upper surface;

a float having a lower surface designed to interfit with the dished upper surface of the weight, wherein the float houses an entrance of the piping, such that when the rainwater from the sump is drained the lower surface of the float shuts off the entrance to the piping and when the rainwater from the sump is not drained the lower surface of the float permits the rainwater to flow into the entrance to the piping.

12. The cover of claim 1, further comprising:

a sump positioned in an open portion of the one or more attachable cover units for collecting rainwater;

a rain catching reservoir positioned higher than the highest point of the slurry container;

a first exit pipe for the sump;

a second exit pipe for the rain catching reservoir coupled to the first exit pipe for the sump;

a tapered plug situated in a tapered exit plug hole and coupled to the first exit pipe for the sump;

a cable attached to the tapered plug;

a float positioned in the sump, wherein one end of the cable is attached to the float and another end of the cable is attached to the first exit pipe for the sump.

13. The cover of claim 1, wherein, for each of the attachable cover units, the attachable portion extends along a length of the at least one edge, and wherein the first attachable cover unit is attached to the second attachable cover unit along the length of the at least one edge of the attachable portion of each of the first and second attachable cover units.

\* \* \* \* \*